United States Patent [19]

Chinn et al.

[11] 4,010,169
[45] Mar. 1, 1977

[54] (E)-4-HYDROXY-11,15-DIOXOPROSTA-8(12),13-DIEN-1-OIC ACID γ-LACTONES

[75] Inventors: Leland J. Chinn, Morton Grove; Karlene W. Salamon, Chicago, both of Ill.

[73] Assignee: G. D. Searle & Co., Chicago, Ill.

[22] Filed: Mar. 10, 1976

[21] Appl. No.: 665,363

[52] U.S. Cl. .............................. 260/343.6; 424/279
[51] Int. Cl.² ........................................ C07D 307/32
[58] Field of Search ................................ 260/343.6

[56] References Cited
OTHER PUBLICATIONS

Klenberg et al., Chem. Abs. 63:2038–2039 (1965).

*Primary Examiner*—Henry R. Jiles
*Assistant Examiner*—C. M. S. Jaisle
*Attorney, Agent, or Firm*—John M. Brown

[57] ABSTRACT

Preparation and the antilipogenic utility of (E)-4-hydroxy-11,15-dioxoprosta-8(12),13-dien-1-oic acid γ-lactones are disclosed.

5 Claims, No Drawings

(E)-4-HYDROXY-11,15-DIOXOPROSTA-8(12),13-DIEN-1-OIC ACID γ-LACTONES

This invention relates to (E)-4-hydroxy-11,15-dioxoprosta-8(12),13-dien-1-oic acid γ-lactones and processes for the preparation thereof. More particularly, this invention provides new, useful, and unobvious prostadienoic acid lactones of the formula

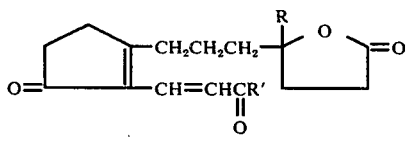

wherein R represents hydrogen or alkyl and R' represents alkyl optionally substituted by halogen.

Among the alkyls represented by R, methyl and ethyl are preferred, whereas the alkyls represented by R' preferably contain more than 4 and fewer than 8 carbons — such as, especially, pentyl and 1,1-dimethylpentyl. However, other monovalent, saturated, acyclic, straight- or branched-chain, hydrocarbon groupings of empirical formula $$-C_nH_{2n+1}$$

wherein $n$ represents a positive integer less than 8 are alkyls likewise within the purview of R and R'. Preferred halogen substituents in the alkyls represented by R' are chlorine and bromine.

The compounds to which this invention relates are useful by reason of their valuable biological properties. Thus, for example, they are antilipogenic.

The antilipogenic utility of the instant compounds can be demonstrated via the following standardized test for their capacity to inhibit the synthesis of lipids from acetate by liver enzymes: Male Charles River CD rats, ordinarily weighing 150–200 g, are individually housed and fed a standard rat diet (Purina Rat Chow) supplemented with 2% DEAE-cellulose for 5 days, whereupon the animals — excluding any which did not eat and/or grown properly during this time — are sacrificed by cervical dislocation, and their livers quickly removed, cooled, blotted, and homogenized gently (to prevent denaturation of the enzymes) in the presence of 2 volumes (2ml per g) of pH 7.4 buffer prepared by mixing monobasic potassium phosphate, dibasic potassium phosphate, magnesium chloride, nicotinamide, and water in amounts sufficient to produce the specified hydrogen ion concentration and make the buffer 0.1 M with respect to total phosphate, 0.004 M with respect to magnesium chloride, and 0.03 M with respect to nicotinamide. The homogenate is promptly centrifuged for 10 minutes at 5000 G and temperatures not to exceed 4° C, the supernatant is decanted, and aliquots thereof are warmed at 37° C for 15 minutes with 2 μmol of NAD, 2 μmol of NADP, and 20 μmol of glucose-6-phosphate dissolved in water, plus test compound dissolved in a solvent which is neither incompatible with the enzymes present nor immiscible with water. The resultant mixture is incubated for 90 minutes at 37° C with 0.1 Ci of sodium acetate-1-$^{14}$C and 10 μmol of unlabeled sodium acetate dissolved in water, the total amount of water incorporated being such that the volume of the incubation mixture is approximately 2.5 ml. Immediately following the incubation, enzymatic biosynthesis is terminated via the modified Dole extraction procedure described in J. Biol. Chem., 234, 2595(1960); and an aliquot of the organic phase is counted via a scintillation detector and appropriate fluor. The resultant count is compared with that from a second procedure identical with the first except for omission of compound solution, and corrections for non-enzymatic uptake of acetate and solvent effects thereon are determined via counts from procedures identical with the first except for substitution of heat-inactivated supernatant in one and omission of compound from the solvent in the other. All tests are carried out in duplicate, and results are expressed as percent inhibition of lipid biosynthesis per unit of supernatant. Compounds are ordinarily tested at an initial concentration of 1 mM, and are considered active if inhibition exceeds 20%. At the 1mM level, (E)-4-hydroxy-11,15-dioxoprosta-8(12),13-dien-1-oic acid γ-lactone, the product of Example 1H hereinafter, effected a 38% inhibition of lipid biosynthesis in the foregoing test. Clofibrate, nafenopin, and probucol inhibited lipid biosynthesis to the extent of 28%, 93%, and 13%, respectively, at the 1 mM level in the test. This activity is specified merely for the purpose of illustration, and is accordingly not to be construed as delimiting or exclusionary.

Those skilled in the art will recognize that observations of activity in standardized tests for particular biological effects are fundamental to the development of valuable new drugs, both veterinary and human.

Preparation of the 4-desalkyl products of this invention proceeds by reducing the zeta carbonyl in 4-methoxy-γ,ζ-dioxobenzeneheptanoic acid [J. Chem. Soc., 1939, 1743] to methylene via low pressure hydrogenation in the presence of palladium black; reducing the γ-carbonyl to hydroxyl in the resultant 4-methoxy-γ-oxobenzeneheptanoic acid by contacting it in cold 2-propanol with sodium tetrahydroborate(1-); subjecting the γ-hydroxy-4-methoxybenzeneheptanoic acid thus obtained to Birch reduction, and lactonizing in situ the γ-hydroxy-4-oxo-1-cyclohexeneheptanoic acid which eventuates by heating it in benzene; contacting the lactone with methanol in the presence of malonic acid to induce ketalization; contacting the ketal in ethanol with ozone and hydrogenating in situ the mixture of ozonide and hydroperoxide so formed, using 5% palladium-on-charcoal as catalyst; and contacting, under nitrogen, a cold 1,2-dimethoxyethane solution of the tetrahydro-β,β-dimethoxy-ε,5-dioxo-2-furannonanal derived thereby with the phosphonium ylid prepared by adding a phosphonate of the formula

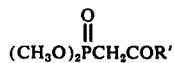

to a sulfinyl bismethane solution of sodium methylsulfinylmethide prepared by mixing a 50% dispersion of sodium hydride in mineral oil with sulfinyl bismethane. The resultant alkenedione

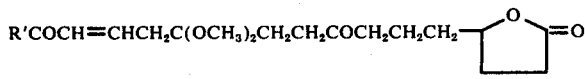

is contacted with dilute hydrochloric acid in dioxane, cleaving the ketal linkages and affording a mixture of alkenetriones

and

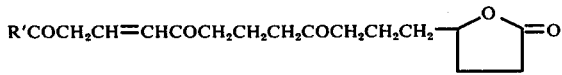

which, on contacting under nitrogen with dilute aqueous sodium hydroxide, are cyclized to a product of the formula

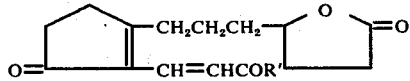

In each of the five formulas immediately preceding, R' retains the meaning originally assigned.

The 4-alkyl products of the invention are prepared by contacting 4-methoxy-γ-oxobenzeneheptanoic acid in either with a Grignard reagent of the formula RMgBr

[R being as originally defined herein] and substituting the resultant γ-alkyl-γ-hydroxy-4-methoxybenzeneheptanoic acid for γ-hydroxy-4-methoxybenzeneheptanoic acid in the procedures starting therewith, outlines above.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. A solution of 10 parts of 4-methoxy-γ,ξ-dioxobenzeneheptanoic acid in 215 parts of 95% ethanol is agitated at 55° under 49 atm of hydrogen in the presence of 3 parts of palladium black for 3 hours, whereupon catalyst is filtered out and solvent removed from the filtrate by vacuum distillation. The residue is crystallized from a mixture of ether and hexane to give 4-methoxy-γ-oxobenzeneheptanoic acid melting at approximately 88°–89°, and having the formula

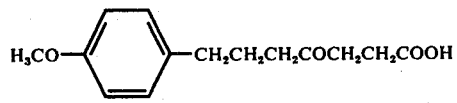

B. To a suspension of 79 parts of 4-methoxy-γ-oxobenzeneheptanoic acid in 630 parts of 2-propanol at 0°–5° is added, with stirring during one-half hour, 80 parts of sodium tetrahydroborate(1—). Stirring is continued at 0°–5° for 3½ hours after the addition is complete, at which point the reaction mixture is consecutively diluted with an equal volume of water and acidified with cold 10% hydrochloric acid. The mixture thus obtained is extracted with cold dichloromethane. The dichloromethane extract is washed with water, dried over anhydrous sodium sulfate, and stripped of solvent by vacuum distillation at temperatures less than 40°. The residue is crystallized from a mixture of cold ether and hexane to give γ-hydroxy-4-methoxybenzeneheptanoic acid melting at approximately 67°–68°, and having the formula

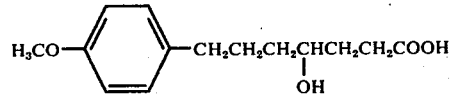

C. To 680 parts of ammonia freshly distilled from sodium is added a solution of 20 parts of γ-hydroxy-4-methoxybenzeneheptanoic acid in 395 parts of absolute 2-propanol. To the resultant mixture is slowly added, portionwise during 10 minutes, 10 parts of lithium. When the reaction mixture turns white, an additional 5 parts of lithium is incorporated portionwise, whereupon the reaction mixture is stirred until it becomes colorless (after approximately 20 minutes). At this point, 120 parts of ethanol followed by 240 parts of water is added. Ammonia is then removed by evaporation; and the residue is consecutively cooled to 0°–5°, acidified with concentrated hydrochloric acid, and extracted with cold dichloromethane. The dichloromethane extract is washed with water, dried over anhydrous sodium sulfate, and stripped of solvent by vacuum distillation. The oily residue is taken up in approximately 475 parts of benzene; and the benzene solution is heated at the boiling point under reflux for 2½ hours, water being removed as formed. Solvent is thereupon removed by vacuum distillation, leaving a pale yellow oil which is taken up in benzene. This benzene solution is chromatographed on silica gel, using benzene and mixtures thereof with increasing amounts of ethyl acetate as developing solvents. From an eluate comprising 20% ethyl acetate in benzene, on evaporation of solvent, tetrahydro-5-[3-(4-oxo-1-cyclohexen-1-yl)propyl]furan-2-one is obtained as the residue, an oil. It has the formula

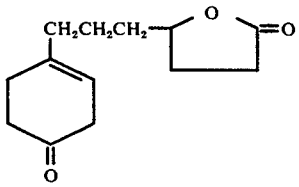

D. To a solution of 41 parts of tetrahydro-5-[3-(4-oxo-1-cyclohexen-1-yl)propyl]furan-2-one in 320 parts of methanol is added a solution of 20 parts of malonic acid in 160 parts of methanol. The resultant mixture is stirred at room temperatures for 7 hours, then cooled to 0°–5° and maintained thereat while being made basic with aqueous 5% sodium bicarbonate. The mixture thus obtained is extracted with ether. The ether extract is washed with water, dried over anhydrous sodium sulfate, and stripped of solvent by vacuum distillation. The residue is taken up in a 50:50 (by volume) mixture of ethyl acetate and hexane, and the resultant solution is filtered through silica gel. Solvent is removed from the filtrate by vacuum distillation, affording tetrahydro-5-[3-(4,4-dimethoxy-1-cyclohexen-1-yl)propyl]furan-2-one as the residue, an oil. It has the formula

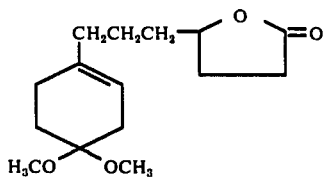

E. Ozone is bubbled through a solution of 50 parts of tetrahydro-5-[3-(4,4-dimethoxy-1-cyclohexen-1-yl)propyl]furan-2-one in 2000 parts of absolute ethanol at 0°–5° until thin layer chromatography indicates that ozonolysis has been effected. The reaction mixture is then flushed with nitrogen, whereupon approximately 6 parts of 5% pallidium-on-charcoal is introduced. The resultant mixture is hydrogenated at 45 atm and 0° for 45 minutes, whereupon catalyst is removed by filtration and the filtrate is stripped of solvent by vacuum distillation. The residue is taken up in benzene, and the benzene solution is dried over anhydrous sodium sulfate. Removal of solvent by vacuum distillation affords tetrahydro-β,β-dimethoxy-ε,5-dioxo-2-furannonanal as the residue, an oil. It has the formula

F. To a mixture of 70 parts of sulfinylbismethane with approximately 2 parts of a 50% dispersion of sodium hydride in mineral oil is added 11 parts of dimethyl (2-oxoheptyl) phosphonate. The resultant mixture is added, with stirring during 1 hour, to a solution of 10 parts of tetrahydro-β,β-dimethoxy-ε,5-dioxo-2-furannonanal in 52 parts of 1,2-dimethoxyethane at 0°–5° under nitrogen. Stirring is continued for 5 minutes longer, whereupon the reaction mixture is poured into 5 volumes of water, and the mixture thus obtained is extracted with benzene. The benzene extract is washed with water, dried over anhydrous sodium sulfate, and stripped of solvent by vacuum distillation. The residue is taken up in a 50:50 (by volume) mixture of ethyl acetate and hexane. The resultant solution is chromatographed on silica gel. Elution with a 75:25 (by volume) mixture of ethyl acetate and hexane affords, upon removal of solvent by vacuum distillation, (E)-1-(tetrahydro-5-oxofuran-2-yl)-7,7-dimethoxyhexadec-9-ene-4,11-dione as the residue, an oil. It has the formula

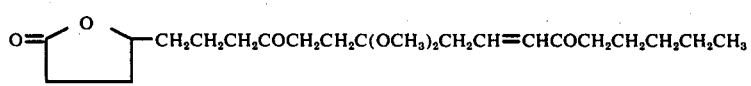

G. To a solution of 44 parts of (E)-1-(tetrahydro-5-oxofuran-2-yl)-7,7-dimethoxyhexadec-9-ene-4,11-dione in 2700 parts of dioxan is added 110 parts of concentrated hydrochloric acid in 11,000 parts of water. The resultant mixture is concentrated by evaporation at room temperatures under approximately 0.01 atm of pressure for 4 hours, whereupon the concentrate is extracted with benzene. The benzene extract is washed with water, dried over anhydrous sodium sulfate, and stripped of solvent by vacuum distillation. The residue is crystallized from a mixture of ether and hexane. The product thus obtained is a mixture of (E)-1-(tetrahydro-5-oxofuran-2-yl)hexadec-8-ene-4,7,11-trione and (E)-1-(tetrahydro-5-oxofuran-2-yl)hexadec-9-ene-4,7,11-trione, which have the formulas

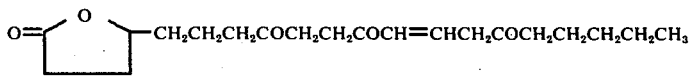

and

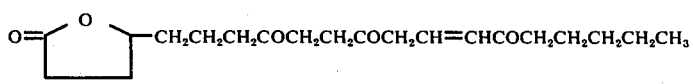

respectively.

H. To a suspension of 8 parts of a mixture of (E)-1-(tetrahydro-5-oxofuran-2-yl)hexadec-8-ene-4,7,11-trione and (E)-1-(tetrahydro-5-oxofuran-2-yl)hexadec-9-ene-4,7,11-trione in 210 parts of water under nitrogen is added 21 parts of aqueous 2% sodium hydroxide. The resultant mixture is stirred for one-half hour at room temperature, then cooled to 0°–5° and acidified thereat with aqueous 2% citric acid. The mixture thus obtained is extracted with dichloromethane.

The dichloromethane extract is washed with water, dried over anhydrous sodium sulfate, and stripped of solvent by vacuum distillation. The residue is taken up in benzene; and the benzene solution is chromatographed on silica gel, using benzene and mixtures thereof with increasing amounts of ethyl acetate as developing solvents. From an eluate comprising 20% ethyl acetate in benzene, on evaporation of solvent and recrystallization of the residue from a mixture of ether and hexane, (E)-4-hydroxy-11,15-dioxoprosta-8(12),13-dien-1-oic acid γ-lactone melting at approximately 55°–56° is obtained. The product has the formula

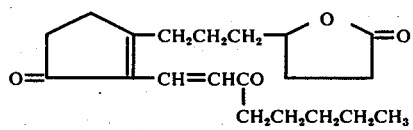

EXAMPLE 2

A. To a cold solution of 18 parts of methyl magnesium bromide in 210 parts of anhydrous ether under nitrogen is slowly added a solution of 25 parts of 4-methoxy-γ-oxobenzeneheptanoic acid in 350 parts of anhydrous ether. The resultant mixture is stirred for 3 hours at room temperatures, then poured into a slight excess of ice-cold 10% hydrochloric acid. The mixture thus obtained is immediately extracted with cold ether. The ether extract is washed with water until the washings are neutral, then dried over anhydrous sodium sulfate, and finally stripped of solvent by vacuum distillation at temperatures not to exceed 40°. The residue is γ-hydroxy-4-methoxy-γ-methylbenzeneheptanoic acid, having the formula

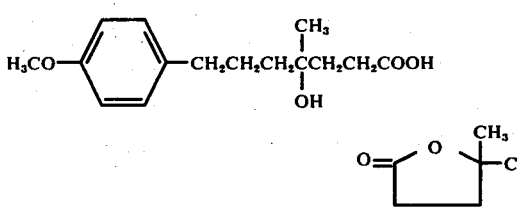

B. Substitution of 20 parts of γ-hydroxy-4-methoxy-γ-methylbenzeneheptanoic acid for the γ-hydroxy-4-methoxybenzeneheptanoic acid called for in Example 1C affords, by the procedure there detailed, tetrahydro-5-methyl-5-[3-(4-oxo-1-cyclohexen-1-yl)propyl]-furan-2-one, having the formula

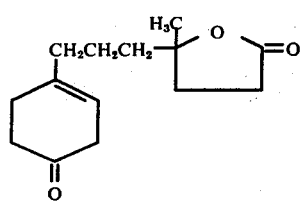

C. Substitution of 41 parts of tetrhydro-5-methyl-5-[3-(4-oxo-1-cyclohexen-1-yl)propyl]furan-2-one for the tetrahydro-5-[3-(4-oxo-1-cyclohexen-1-yl)propyl]-furan-2-one called for in Example 1D affords, by the procedure there detailed, tetrahydro-5-[3-(4,4-dimethoxy-1-cyclohexen-1-yl)propyl]-5-methylfuran-2-one, having the formula

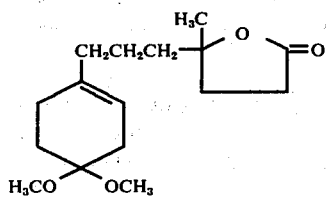

D. Substitution of 50 parts of tetrahydro-5-[3-(4,4-dimethoxy-1-cyclohexen-1-yl)propyl]-5-methylfuran-2-one for the tetrahydro-5-[3-(4,4-dimethoxy-1-cyclohexen-1-yl)propyl]furan-2-one called for in Example 1E affords, by the procedure there detailed, tetrahydro-β,β-dimethoxy-2-methyl-ε,5-dioxo-2-furannonanal, having the formula

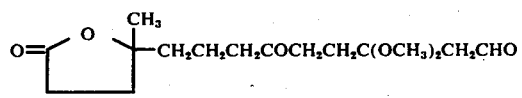

E. Substitution of 10 parts of tetrahydro-β,β-dimethoxy-2-methyl-ε,5-dioxo-2-furannonanal for the tetrahydro-β,β-dimethoxy-ε,5-dioxo-2-furannonanal called for in Example 1F affords, by the procedure there detailed, (E)-1-(tetrahydro-2-methyl-5-oxofuran-2-yl)-7,7-dimethoxyhexadec-9-ene-4,11-dione, having the formula

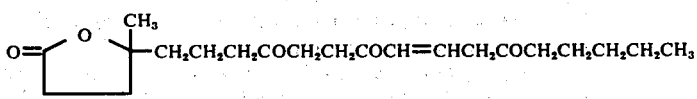

F. Substitution of 44 parts of (E)-1-(tetrahydro-2-methyl-5-oxofuran-2-yl)-7,7-dimethoxyhexadec-9-ene-4,11-dione for the (E)-1-(tetrahydro-5-oxofuran-2-yl)-7,7-dimethoxyhexadec-9-ene-4,11-dione called for in Example 1G affords, by the procedure there detailed, a mixture of (E)-1-(tetrahydro-2-methyl-5-oxofuran-2-yl)hexadec-8-ene-4,7,11-trione and (E)-1-(tetrahydro-2-methyl-5-oxofuran-2-yl)hexadec-9-ene-4,7,11-trione, which have the formulas and

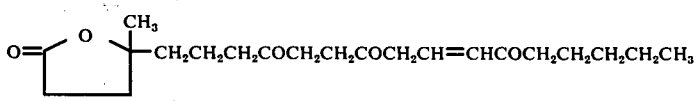

respectively.

G. Substitution of 8 parts of the mixture of (E)-1-(tetrahydro-2-methyl-5-oxofuran-2-yl)hexadec-8-ene-4,7,11-trione and (E)-1-(tetrahydro-2-methyl-5-oxofuran-2-yl)hexadec-9-ene-4,7,11-trione for the mixture of (E)-1-(tetrahydro-5-oxofuran-2-yl)hexadec-8-ene-4,7,11-trione and (E)-1-(tetrahydro-5-oxofuran-2-yl)hexadec-9-ene-4,7,11-trione called for in Example 1H affords, by the procedure there detailed, (E)-4-hydroxy-4-methyl-11,15-dioxoprosta-8(12),13-dien-1-oic acid γ-lactone. The product has the formula

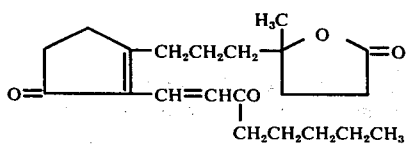

EXAMPLE 3

A. Substitution of 20 parts of ethyl magnesium bromide for the methyl magnesium bromide called for in Example 2A affords, by the procedure called for therein, γ-ethyl-γ-hydroxy-4-methoxybenzeneheptanoic acid, having the formula

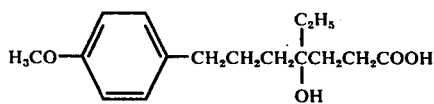

B. Substitution of 20 parts of γ-ethyl-γ-hydroxy-4-methoxybenzeneheptanoic acid for the γ-hydroxy-4-methoxybenzeneheptanoic acid called for in Example 1C affords, by the procedure there detailed, 5-ethyltetrahydro-5-[3-(4-oxo-1-cyclohexen-1-yl)propyl]furan-2-one.

C. Substitution of 41 parts of 5-ethyltetrahydro-5-[3-(4-oxo-1-cyclohexene-1-yl)propyl]furan-2-one for the tetrahydro-5-[3-(4-oxo-1cyclohexen-1-yl)propyl]furan-2-one called for in Example 1D affords, by the procedure there detailed, 5-ethyltetrahydro-5-[3-(4,4,-dimethoxy-1-cyclohexen-1-yl)propyl]furan-2-one.

D. Substitution of 50 parts of 5-ethyltetrahydro-5-[3-(4,4-dimethoxy-1-cyclohexen-1-yl)propyl]furan-2-one for the tetrahydro-5-[3-(4,4-dimethoxy-1-cyclohexen-1-yl)-propyl]furan-2-one called for in Example 1E affords, by the procedure there detailed 2-ethyltetrahydro-β,β-dimethoxy-ε,5-dioxo-2-furannonanal.

E. Substitution of 10 parts of 2-ethyltetrahydro-β,β-dimethoxy-ε,5-dioxo-2-furannonanal for the tetrahydro-β,β-dimethoxy-ε,5-dioxo-2-furannonanal called for in Example 1F affords, by the procedure there detailed, (E)-1-(2-ethyltetrahydro-5-oxofuran-2-yl)-7,7-dimethoxyhexadec-9-ene-4,11-dione.

F. Substitution of 44 parts of (E)-1-(2-ethyltetrahydro-5-oxofuran-2-yl)-7,7-dimethoxyhexadec-9-ene-4,11-dione for the (E)-1-(tetrahydro-5-oxofuran-2-yl)-7,7-dimethoxyhexadec-9-ene-4,11-dione called for in Example 1G affords, by the procedure there detailed, a mixture of (E)-1-(2-ethyltetrahydro-5-oxofuran-2-yl)hexadec-8-ene-4,7,11-trione and (E)-1-(2-ethyltetrahydro-5-oxofuran-2-yl)hexadec-9-ene-4,7,11-trione.

G. Substitution of 8 parts of a mixture of (E)-1-(2-ethyltetrahydro-5-oxofuran-2-yl)hexadec-8-ene-4,7,11-trione and (E)-1-(2-ethyltetrahydro-5-oxofuran-2-yl)hexadec-9-ene-4,7,11-trione for the mixture of (E)-1-(tetrahydro-5-oxofuran-2-yl)hexadec-8-ene-4,7,11-trione and (E)-1-tetrahydro-5-oxofuran-2-yl)hexadec-9-ene-4,7,11-trione called for in Example 1H affords, by the procedure there detailed, (E)-4-ethyl-4-hydroxy-11,15-dioxoprosta-8(12),13-dien-1-oic acid γ-lactone. The product has the formula

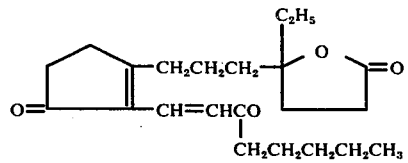

EXAMPLE 4

A. Substitution of approximately 13 parts of dimethyl 3,3-dimethyl-2-oxoheptyl phosphonate [Prostaglandins, 4, 143(1973)] for the dimethyl 2-oxoheptyl phosphonate called for in Example 1F affords, by the procedure there detailed, (E)-1-(tetrahydro-5-oxofuran-2-yl)-7,7-dimethoxy-12,12-dimethylhexadec-9-ene-4,11-dione, having the formula

B. Substitution of 44 parts of (E)-1-(tetrahydro-5-oxofuran-2-yl)-7,7-dimethoxy-12,12-dimethylhexadec-9-ene-4,11-dione for the (E)-1-(tetrahydro-5-oxofuran-2-yl)-7,7-dimethoxyhexadec-9-ene-4,11-dione called for in Example 1G affords, by the procedure there detailed, (E)-1-(tetrahydro-5-oxofuran-2yl)-12,12-dimethylhexadec-8-ene-4,7,11-trione and (E)-1-(tetrahydro-5-oxofuran-2-yl)-12,12-dimethylhexadec-9-ene-4,7,11-trione.

C. Substitution of 8 parts of a mixture of (E)-1-(tetrahydro-5-oxofuran-2-yl)-12,12-dimethylhexadec-8-ene-4,7,11-trione and (E)-1-(tetrahydro-5-oxofuran-2-yl)-12,12-dimethylhexadec-9-ene-4,7,11-trione for the mixture of (E)-1-(tetrahdyro-5-oxofuran-2-yl)hexadec-8-ene-4,7,11-trione and (E)-1-(tetrahydro-5-oxofuran-2-yl)hexadec-9-ene-4,7,11-trione called for in Example 1H affords, by the procedure there detailed, (E)-4-hydroxy-16,16-dimethyl-11,15-dioxoprosta-8(12),13-dien-1-oic acid γ-lactone. The product has the formula

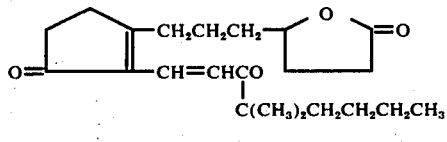

What is claimed is:
1. A compound of the formula

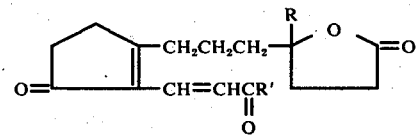

wherein R represents hydrogen, methyl, or ethyl and R' represents alkyl containing more than 4 and fewer than 8 carbons.

2. A compound according to claim 1 having the formula

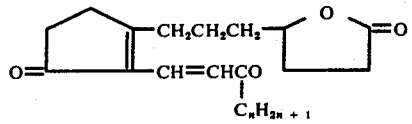

wherein $n$ represents a positive integer greater than 4 and less than 8.

3. A compound according to claim 1 which is (E)-4-hydroxy-11,15-dioxoprosta-8(12),13-dien-1-oic acid γ-lactone.

4. A compound according to claim 1 having the formula

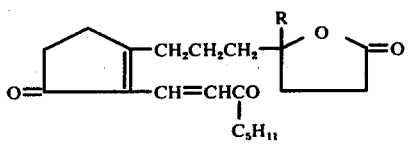

wherein R represents methyl or ethyl.

5. A compound according to claim 1 which is (E)-4-hydroxy-4-methyl-11,15-dioxoprosta-8(12),13-dien-1-oic acid γ-lactone.

* * * * *

UNITED STATES PATENT AND TRADEMARK OFFICE
CERTIFICATE OF CORRECTION

PATENT NO. : 4,010,169
DATED : March 1, 1977
INVENTOR(S) : Leland J. Chinn and Karlene W. Salamon It is certified that error appears in the above—identified patent and that said Letters Patent are hereby corrected as shown below:

Column 3, line 33, "either" should read -- ether --.

Column 3, line 39, "outlines" should read -- outlined --.

Column 5, line 48, "pallidium" should read -- palladium --.

Column 3, 3rd formula,

"$R'COCH_2CH=CHCOCH_2CH_2CH_2COCH_2CH_2CH_2$" should read

-- $R'COCH_2CH=CHCOCH_2CH_2COCH_2CH_2CH_2$ --.

Signed and Sealed this

*Twenty-seventh* Day of *September 1977*

[SEAL]

Attest:

RUTH C. MASON
*Attesting Officer*

LUTRELLE F. PARKER
*Acting Commissioner of Patents and Trademarks*